US007507813B2

(12) United States Patent
Chen et al.

(10) Patent No.: US 7,507,813 B2

(45) Date of Patent: Mar. 24, 2009

(54) AMORPHOUS CEFUROXIME AXETIL AND PREPARATION PROCESS THEREFORE

(75) Inventors: Jianfeng Chen, Beijing (CN); Jie Zhong, Beijing (CN); Zhigang Shen, Beijing (CN); Jiyao Zhang, Beijing (CN)

(73) Assignees: Nanomaterials Technology Pte Ltd., Singapore (SG); Beijing University of Chemical Technology, Beijing (CN)

( * ) Notice: Subject to any disclaimer, the term of this patent is extended or adjusted under 35 U.S.C. 154(b) by 484 days.

(21) Appl. No.: 11/187,555

(22) Filed: Jul. 22, 2005

(65) Prior Publication Data

US 2006/0020130 A1 Jan. 26, 2006

(30) Foreign Application Priority Data

Jul. 22, 2004 (CN) ........................ 2004 1 0069398

(51) Int. Cl.
*C07D 501/34* (2006.01)

(52) U.S. Cl. ....................................... 540/220; 540/222

(58) Field of Classification Search .................. 540/222
See application file for complete search history.

(56) References Cited

U.S. PATENT DOCUMENTS

| | | | | |
|---|---|---|---|---|
| 4,562,181 | A * | 12/1985 | Crisp et al. | 514/202 |
| 4,775,750 | A * | 10/1988 | White et al. | 540/222 |
| 4,820,833 | A | 4/1989 | Crisp et al. | |
| 4,826,689 | A * | 5/1989 | Violanto | 424/489 |
| 5,013,833 | A | 5/1991 | Crisp et al. | |
| 5,498,787 | A * | 3/1996 | Wang et al. | 540/222 |
| 5,677,443 | A * | 10/1997 | Zenoni et al. | 540/215 |
| 5,847,118 | A * | 12/1998 | Karimian et al. | 540/222 |
| 6,060,599 | A * | 5/2000 | Somani et al. | 540/222 |
| 6,346,530 | B1 * | 2/2002 | Somani et al. | 514/226.8 |
| 6,384,213 | B1 * | 5/2002 | Handa et al. | 540/222 |
| 6,534,494 | B1 * | 3/2003 | Somani et al. | 514/202 |
| 6,833,452 | B2 * | 12/2004 | Tyagi et al. | 540/222 |
| 2004/0077850 | A1 * | 4/2004 | Kansal et al. | 540/228 |
| 2004/0210050 | A1 * | 10/2004 | Felisi et al. | 540/228 |
| 2004/0242864 | A1 * | 12/2004 | Longoni et al. | 540/222 |

FOREIGN PATENT DOCUMENTS

| | | | | |
|---|---|---|---|---|
| CN | 1020036 | C | | 3/1993 |
| CN | 1021546 | C | | 7/1993 |
| CN | 1036766 | C | | 12/1997 |
| CN | 1038578 | C | | 6/1998 |
| CN | 1199735 | | * | 11/1998 |
| CN | 1285365 | A | | 2/2001 |
| CN | 1112320 | C | | 6/2003 |
| CN | 1447812 | A | | 10/2003 |
| CN | 1473833 | A | | 2/2004 |
| GB | 1571683 | | | 7/1980 |
| GB | 2145409 | | * | 3/1985 |
| WO | WO 9843980 | A1 | * | 10/1998 |
| WO | WO 99/65919 | | | 12/1999 |
| WO | WO 01/87893 | | | 11/2001 |
| WO | WO0216382 | A1 | * | 2/2002 |
| WO | WO03024977 | | * | 3/2003 |

OTHER PUBLICATIONS

Bilati, European Journal of Pharmaceutical Sciences vol. 24, Issue 1, Jan. 2005, pp. 67-75.*

Krause, International Journal of Pharmaceutics vol. 214, Issues 1-2, Feb. 19, 2001, pp. 21-24.*

Chen, Jian-feng et al., Feasibility of preparing nanodrugs by high-gravity reactive precipitation, 2004, International Journal of Pharmaceutics, vol. 269, No. , pp. 267-274.

Shen Zhi-Gang et al,, "Properties of Cephradine Produced by High Gravity Technology," 2004, Chin. Pharm. J., vol. 39, No. 1, 36-39. (Abstract).

Sasinowska-Motyl, et al., "Esters of cephalosporins. Part I. Permeability of cefuroxime liberated from its 1-acetoxyethyl ester through biological membranes; influence of the form and size of the ester particles," 1995, Acta Poloniae Pharmaceutica, Polish Pharmaceutical Society, vol. 52, No. 5, 391-395.

Oszczapowicz, et al., "Esters of cephalosporins. Part II. Differences in the properties of various forms of the 1-acetoxyethyl ester of cefuroxime," 1995, Acta Poloniae Pharmaceutica, Polish Pharmaceutical Society, vol. 52, No. 5, 397-401.

* cited by examiner

*Primary Examiner*—Mark L Berch
(74) *Attorney, Agent, or Firm*—Townsend and Townsend and Crew LLP

(57) ABSTRACT

A novel process for the preparation of amorphous cefuroxime axetil particles and the amorphous cefuroxime axetil particles therefrom are disclosed in the invention. Specifically, the invention is implemented by means of antisolvent recrystallization to prepare the cefuroxime axetil in an amorphous form; particularly, the amorphous ultrafine or even nanosized cefuroxime axetil with a controllable particle size and a narrow particle size distribution. The cefuroxime axetil according to the invention can used to enhance bioavailability, since it is in an amorphous form and has a controllable particle size and a narrow particle size distribution.

8 Claims, 8 Drawing Sheets

AMORPHOUS CEFUROXIME AXETIL AND PREPARATION PROCESS THEREFORE

FIELD OF THE INVENTION

This invention relates to a bioavailable amorphous cefuroxime axetil and a preparation process therefore.

BACKGROUND OF THE INVENTION

Cefuroxime axetil, i.e. (6R,7R)-3-carbamoyloxymethyl-7-[(Z)-2-(fur-2-yl)-2-methoxyimino-acetylamido]-ceph-3-em-4-carboxylic acid 1-acetoxyethyl ester, is 1-acetoxyethyl ester of cefuroxime. A broad spectrum, second generation cephalosporin, cefuroxime axetil is taken by mouth and has good antibiotic activity against both gram-positive and gram-negative microorganisms. The structure of the compound is as follows:

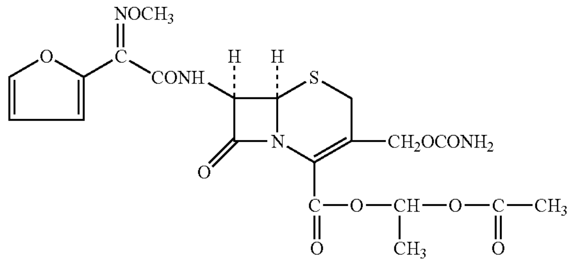

Cefuroxime axetil is present in two forms: crystalline and amorphous. GB 1,571,683 A1 discloses the process for the preparation of crystalline cefuroxime axetil. The crystalline cefuroxime axetil does not possess the necessary bioavailability characteristics associated with the amorphous form. It is known that orally administered cephalosporin (and medicaments in general) must be in a form of highly bioavailability. For this reason, commercially available cefuroxime axetil which is registered throughout the world is in a substantially amorphous form, since cefuroxime axetil in a substantially amorphous form has a higher bioavailability for oral administration than that in a crystalline form, as disclosed in U.S. Pat. No. 4,820,833 (the '833 patent).

The '833 patent describes a process for the preparation of amorphous cefuroxime axetil, in which amorphous cefuroxime axetil is obtained by spray drying a solution of cefuroxime axetil of a crystalline form in an organic solvent. The current process for industrializing amorphous cefuroxime axetil is usually the spray drying techniques as described in the '833 patent. However, the disadvantages associated with those techniques are that, for example, the cost in equipments may be high, recycling the organic solvents may be difficult, and improper temperature control during the drying process may affect the quality of the cefuroxime axetil.

U.S. Pat. No. 5,013,833 discloses a process for preparing amorphous cefuroxime axetil by the spray drying techniques or by solvent precipitation. Neither an amorphous cefuroxime axetil particle with controllable particle size, nor an ultrafine or even nanosized amorphous cefuroxime axetil particle can be produced by the methods described in U.S. Pat. No. 5,013,833. Furthermore, solvent precipitation which is carried out within the conventional stirred vessels does have some disadvantages, e.g. non-uniform mixing and local supersaturation, which may have an influence on the quality of the cefuroxime axetil powder.

Consequently, the present invention is directed to provide a process for the preparation of an ultrafine or nanosized amorphous cefuroxime axetil particle. Specifically, the invention provides a process for the preparation of an cefuroxime axetil particle having both controllable average particle size and narrow particle size distribution.

SUMMARY OF THE INVENTION

Based on the techniques in the prior art, it has been found by the present inventors that amorphous cefuroxime axetil can be obtained by, within a high-gravity reactor, mixing a cefuroxime axetil solution with an antisolvent in which cefuroxime axetil is insoluble, or alternatively by, within a stirred reactor, mixing the cefuroxime axetil solution and the antisolvent via two different atomizers for the solution and the antisolvent; then precipitating and crystallizing.

Specifically, the present invention provides a process for the preparation of ultrafine or nanosized amorphous cefuroxime axetil, which comprises the steps of:

(1) providing a cefuroxime axetil solution and an appropriate antisolvent;

(2) feeding the cefuroxime axetil solution and the antisolvent substantially simultaneously into a high-gravity reactor via a first inlet for the cefuroxime axetil solution and a second inlet for the antisolvent, respectively; or alternatively by spraying the cefuroxime axetil solution via an atomizer into a stirred reactor in which the antisolvent is contained, thereby precipitating and crystallizing the cefuroxime axetil by means of antisolvent recrystallization;

(3) collecting the slurry of the cefuroxime axetil obtained in step (2); and (4) filtering and then drying the slurry to obtain the ultrafine or nanosized cefuroxime axetil powder in an amorphous form.

The invention further provides an amorphous form of cefuroxime axetil powder produced by the process according to the invention, which comprises ultrafine or nanosized cefuroxime axetil particles having a narrow particle size distribution, preferably at least 70% of cefuroxime axetil particles having an average particle size of the same order.

The invention also provides an amorphous cefuroxime axetil particle having X-ray diffraction spectra as disclosed below in the Detailed Description.

During the process of precipitating and crystallizing according to the invention, the solution and the antisolvent are contacted with each other sufficiently and uniformly, thereby achieving ultra-speed molecular micro-mixing, leading to overcome the limitations of non-uniform and insufficient mixing between the solution and the antisolvent, and avoid the typical local supersaturation associated with the known methods. Since the reactants are contacted and mixed sufficiently and uniformly according to the process of the invention, the precipitation time is decreased and the yield ratio is increased compared with those processes in the prior art. Furthermore, less space is required in the invention, hence favoring mass production.

DETAILED DESCRIPTION OF THE INVENTION

The first aspect of the invention provides a process for the preparation of ultrafine cefuroxime axetil in an amorphous form, which comprises the steps of:

(1) providing a cefuroxime axetil solution and an appropriate antisolvent;

(2) feeding the cefuroxime axetil solution and the antisolvent into a high-gravity reactor via a first inlet for the cefuroxime axetil solution and a second inlet for the antisolvent, respectively; or alternatively by spraying the solution via an atomizer into a stirred reactor in which the antisolvent is contained, thereby precipitating and crystallizing the cefuroxime axetil by means of antisolvent recrystallization;

(3) collecting the slurry of cefuroxime axetil obtained in step (2); and (4) filtering and then drying the slurry to obtain the ultrafine or nanosized cefuroxime axetil powder in an amorphous form.

The term “crystallization” herein refers to the general “crystallization” and “recrystallization” processes, and it means the recovery of cefuroxime axetil particles by means of crystallization or recrystallization from any solution which contains cefuroxime axetil, including, for example, a solution of cefuroxime axetil in ethyl acetate, a solution of cefuroxime axetil in acetone, a solution of cefuroxime axetil in chloroform, or a mixed solution of cefuroxime axetil in the above-mentioned solvents.

According to the invention, the antisolvent can be any solvent which is able to be mutually or partially miscible with the solution of cefuroxime axetil, and has solubility as low as possible to the cefuroxime axetil. Preferably, the antisolvent comprises methyl tert-butyl ether, ethyl ether, isopropyl ether, n-hexane, water and the like.

The “high-gravity rotary bed” in this invention comprises the high-gravity rotary packed beds which are well-known and generally used in this art. Hence, the two terms of “high-gravity rotary packed bed” and “high-gravity rotary bed” can be used interchangeably. The high-gravity rotary packed beds include, for example, those described and claimed in Chinese patent ZL 95107423.7, Chinese patent ZL 92100093.6, Chinese patent ZL 91109255.2, Chinese patent ZL 95105343.4, Chinese patent application 00100355.0, and Chinese patent application 00129696.5, which are incorporated herein by reference in their entirety.

Figure 1:
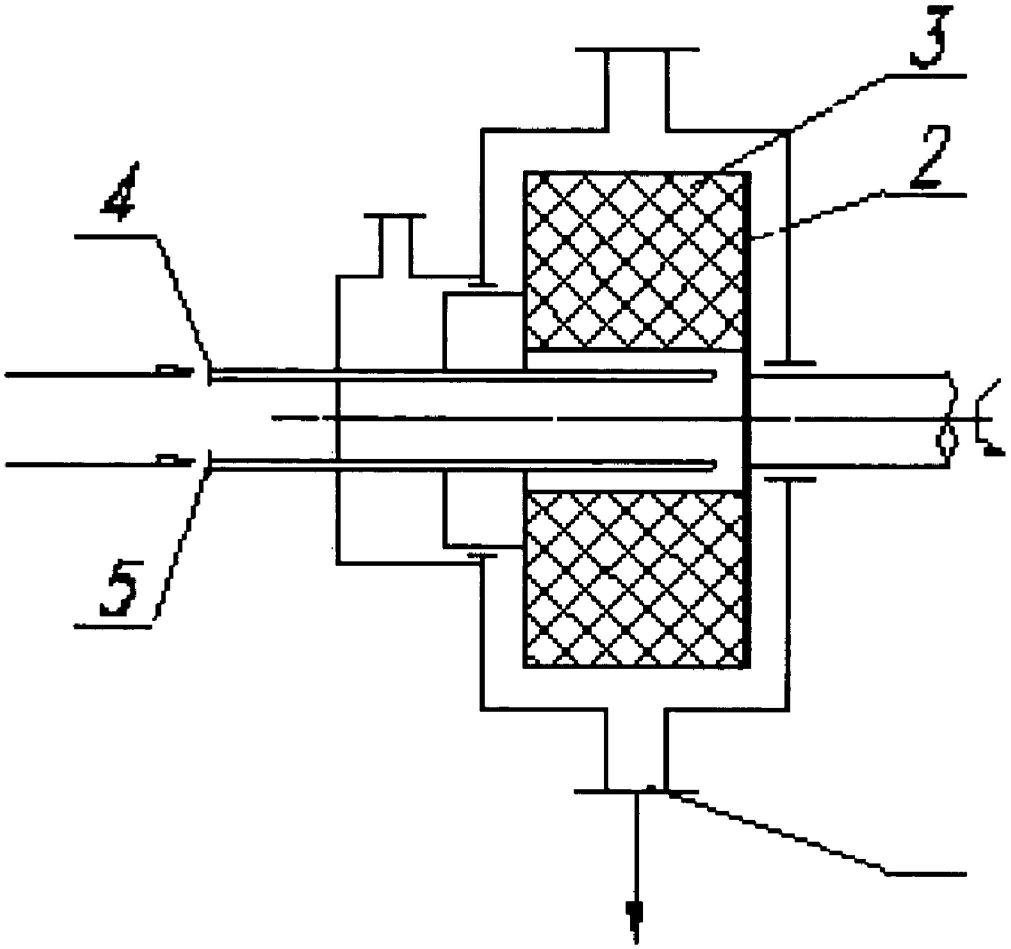
FIG. 1 shows a schematic representation of the high-gravity reactor for preparation of the amorphous cefuroxime axetil according to one embodiment of the present invention.

The high-gravity reactor used in this invention includes the usual rotary packed bed and the unpacked porthole high-gravity reactor having a porthole, such as screwed porthole and flat porthole inside its rotor. The high-gravity reactor comprises a reactant outlet 1, a rotor 2, a packing layer 3, a liquid inlet 4, a reactor casing, a liquid distributor, and a gas inlet 5, as illustrated in FIG. 1. The reactant feed is fed into the high-gravity reactor via the liquid distributor, and is sprayed into tiny droplets within the packing layer, and is uniformly mixed rapidly there.

The packing which is used in the high-gravity reactor of the present invention can include, but is not limited to, metal or non-metal materials, such as screen, perforated plate, corrugated plate, foam material, and structured packing.

The high-gravity reactor of the present invention has a rotor which usually rotates at a speed of at least between about 100 rpm to about 10,000 rpm, preferably between about 500 rpm to about 5000 rpm, and more preferably between about 1000 rpm to about 3000 rpm. According to the invention, the average particle size of the resultant cefuroxime axetil can be adjusted by regulating the rotating speed of the rotor in the reactor. Although not bound to any theory, those skilled in the art should understand that the higher the rotating speed of the high-gravity reactor is, the smaller the average particle size of the resultant powder is, and vice versa. However, the reaction is usually carried out in the preferred range of rotating speed of the rotor, due to economic reasons, such as the cost of energy consumption.

The micro-mixing and micro-mass-transfer of the fluids within the high-gravity reactor is greatly enhanced by the use of the reactor, and thus a uniform concentration distribution is obtained, thereby producing unexpected effects which otherwise can not be obtained in the field of normal earth gravity. For instance, the reaction time is reduced by 4 to 100 times, depending on the intrinsic reaction speed of the reaction system, hence dramatically improving the production efficiency; the production capacity of a unit volume of the reactor in a unit time is enhanced by a times of from tens to hundreds, hence greatly reducing energy consumption; and the particle size of the ultrafine powder is also improved. In addition, due to the uniform mixing, the compositions within the particles tends to be easily homogenized, thus improving the quality and grade of the powder.

The atomizer used in the invention generally can be any atomizer used in the art. For example, an atomizer comprising a stationary spray nozzle with a small orifice can be used, in which the spray nozzle is placed at the center of a high-speed packed rotor. Ultrafine atomized liquid droplets can be obtained by spraying the liquid feed out of the orifice of the spray nozzle with a certain speed, and then shearing and atomizing by the high-speed rotary packing layer.

The disadvantages associated with the conventional stirred vessel reactors are that the quality of the product is affected by local supersaturation, which is due to liquid feed can not be uniformly and rapidly mixed at each part of the reactor, upon entering into the reactor. In the present invention, the liquid feed can be atomized into ultrafine droplets immediately after the liquid is fed via the atomizer, and upon entering into the reactor the liquid can be more rapidly and uniformly mixed with the solution (or the solvent) in the reactor, thereby avoiding any local supersaturation and thus improving the quality of the desired product. In addition, since the reactants are contacted and mixed sufficiently and uniformly, the precipitation time is decreased and the yield ratio is increased compared with other processes in the prior art. Furthermore, particles having a smaller and more uniform particle size can be obtained due to the reaction (precipitating and crystallizing) of the atomized droplets in the reactor. Consequently, the size of the particles can be controlled by adjusting the size of the orifice of the nozzle.

Alternatively, the solution of cefuroxime axetil and the antisolvent can be sprayed into the stirred reactor via different atomizers. In addition, it is possible to obtain ultrafine cefuroxime axetil particles with a controllable and uniform average particle size, particularly ultrafine cefuroxime axetil particles with a controllable average particle size and a narrow particle size distribution, by appropriately adjusting the operating parameters of the stirred vessel reactor or high-gravity reactor, such as the rotating speed of the stirred vessel or the rotating speed of the rotor in the high-gravity reactor, and the size of the nozzle. Typically the stirred reactor operates at a stirred speed ranging from between about 50 rpm to about 10,000 rpm. The particles prepared according to the process of the present invention can be used in the forms of tablet and capsule in the pharmaceutical field, since the particles have a uniform particle size, unlike prior art particles having non-uniform size due to the non-uniform stirring associated with the techniques of the prior art. Furthermore, the particles, due to their small and uniform particle size, can be easily formulated into tablet and capsule and have a higher bioavailability.

In the method described above, the solution of cefuroxime axetil and the antisolvent simultaneously are fed into the high-gravity reactor or sprayed into the stirred reactor via different atomizers.

The cefuroxime axetil solution used in the present invention includes any solution of cefuroxime axetil formed by dissolving the crystalline cefuroxime axetil as obtained in any appropriate solvent.

Commonly used solvents in the cefuroxime axetil solution can include, as a non-limiting example, methanol, dichloromethane, chloroform, ethyl acetate, N,N-dimethyl formamide, formic acid, acetic acid, dioxane, acetone, dimethyl sulfoxide or mixtures thereof. Those skilled in the art may choose any other solvents which can be used to dissolve cefuroxime axetil. As used herein, the term “dissolve” means that a clear solution is obtained by dissolving cefuroxime axetil in a solvent. The concentration of the cefuroxime axetil solution is not specially limited, as long as it can meet the requirement of dissolution.

The antisolvent used in the invention typically comprises methyl tert-butyl ether, isopropyl ether, ethyl ether, n-hexane, water and the like, preferably methyl tert-butyl ether, isopropyl ether, ethyl ether, and n-hexane.

According to the process of the present invention, cefuroxime axetil particles with the desired narrow particle size distribution can be obtained by adjusting the reaction conditions, e.g., the rotating speed of the stirred vessel, stirred reactor or high-gravity reactor, reaction temperature, and the flow rates of the solution and antisolvent. Thus, the present invention provides cefuroxime axetil particles with a uniform particle size distribution, specially ultrafine or even nano-sized cefuroxime axetil particles. Specifically, the present invention provides ultrafine cefuroxime axetil particles with an average particle size of usually less than about 100 μm, preferably in the range between about 50 μm and about 20 nm, more preferably in the range between about 10 μm and about 20 nm, and still more preferably in the range between about 5 μm and about 20 nm.

Amorphous cefuroxime axetil particles with a narrow particle size distribution can be obtained by adjusting the reaction conditions (e.g., rotating speed, temperature and flow rate). The particles obtained by the methods described herein differ from those obtained by prior art techniques in that the former has a narrow particle size distribution; that is, at least about 50%, preferably about 70%, and more preferably about 90% of the particles are present in the same order of particle size ranges, such as a particle size distribution of from between about 10 nm to about 100 nm, from between about 200 nm to about 500 nm, from between about 1 μm to about 5 μm, and from between about 5 μm to about 10 μm.

The cefuroxime axetil powders obtained by the method of the present invention have a purity of above 98%, and no less than 75% in terms of dry basis, as determined by HPLC (High Performance Liquid Chromatography).

Figure 2:
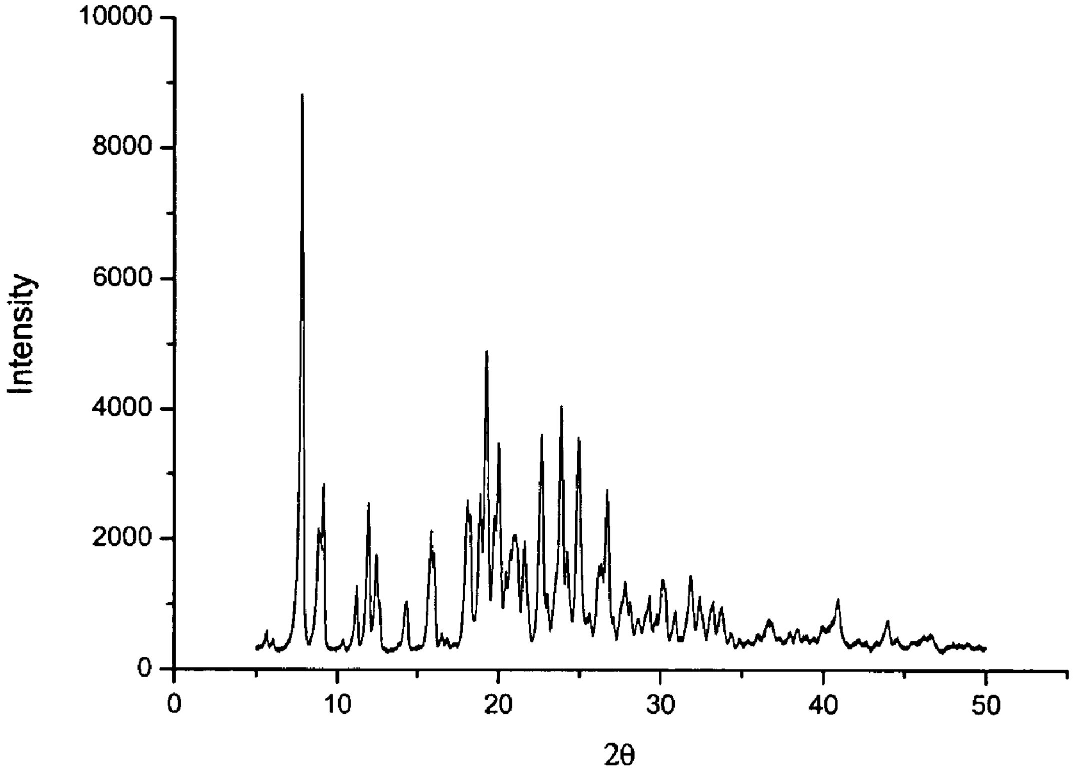
FIG. 2 shows X-ray diffractive spectrum of the crystalline cefuroxime axetil prepared by a conventional method.
Figure 3:
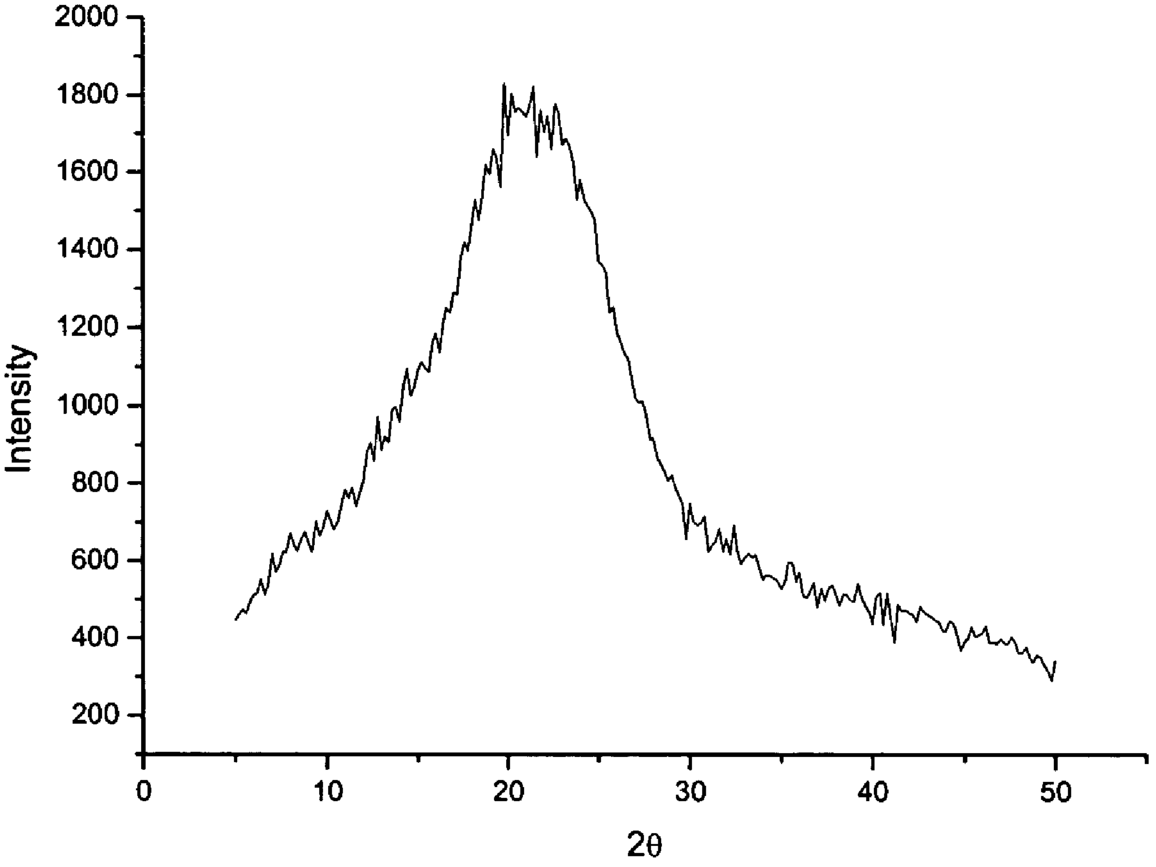
FIG. 3 shows X-ray diffractive spectrum of the amorphous cefuroxime axetil prepared by the chloroform-isopropyl ether system according to the present invention.

Unlike the crystalline cefuroxime axetil typically produced by the prior art which has the X-ray diffractive spectrum shown in FIG. 2, the amorphous cefuroxime axetil particles of the present invention have the X-ray diffractive spectrum shown in FIG. 3. The data of X-ray diffractive analysis is shown in Table 1.

TABLE 1

The X-ray diffractive spectrum of amorphous cefuroxime axetil obtained in the present invention:

| Angle (2θ) | Intensity |
|---|---|
| 5 | 445 |
| 5.2 | 460 |
| 5.4 | 474 |
| 5.6 | 463 |
| 5.8 | 491 |
| 6 | 512 |
| 6.2 | 517 |
| 6.4 | 553 |
| 6.6 | 511 |
| 6.8 | 540 |
| 7 | 620 |
| 7.2 | 570 |
| 7.4 | 586 |
| 7.6 | 625 |
| 7.8 | 621 |
| 8 | 674 |
| 8.2 | 639 |
| 8.4 | 625 |
| 8.6 | 656 |
| 8.8 | 676 |
| 9 | 644 |
| 9.2 | 622 |
| 9.4 | 703 |
| 9.6 | 663 |
| 9.8 | 688 |
| 10 | 730 |
| 10.2 | 706 |
| 10.4 | 681 |
| 10.6 | 701 |
| 10.8 | 741 |
| 11 | 786 |
| 11.2 | 762 |
| 11.4 | 791 |
| 11.6 | 741 |
| 11.8 | 774 |
| 12 | 806 |
| 12.2 | 882 |
| 12.4 | 906 |
| 12.6 | 857 |
| 12.8 | 973 |
| 13 | 885 |
| 13.2 | 923 |
| 13.4 | 905 |
| 13.6 | 989 |
| 13.8 | 998 |
| 14 | 959 |
| 14.2 | 1042 |
| 14.4 | 1096 |
| 14.6 | 1025 |
| 14.8 | 1047 |
| 15 | 1091 |
| 15.2 | 1112 |
| 15.4 | 1098 |
| 15.6 | 1085 |
| 15.8 | 1161 |
| 16 | 1187 |

TABLE 1-continued

The X-ray diffractive spectrum of amorphous cefuroxime axetil obtained in the present invention:

| Angle (2θ) | Intensity |
|---|---|
| 16.2 | 1135 |
| 16.4 | 1207 |
| 16.6 | 1250 |
| 16.8 | 1237 |
| 17 | 1291 |
| 17.2 | 1281 |
| 17.4 | 1379 |
| 17.6 | 1420 |
| 17.8 | 1396 |
| 18 | 1463 |
| 18.2 | 1530 |
| 18.4 | 1476 |
| 18.6 | 1539 |
| 18.8 | 1620 |
| 19 | 1594 |
| 19.2 | 1662 |
| 19.4 | 1639 |
| 19.6 | 1562 |
| 19.8 | 1830 |
| 20 | 1694 |
| 20.2 | 1804 |
| 20.4 | 1755 |
| 20.6 | 1767 |
| 20.8 | 1756 |
| 21 | 1742 |
| 21.2 | 1769 |
| 21.4 | 1821 |
| 21.6 | 1641 |
| 21.8 | 1761 |
| 22 | 1704 |
| 22.2 | 1746 |
| 22.4 | 1660 |
| 22.6 | 1777 |
| 22.8 | 1755 |
| 23 | 1669 |
| 23.2 | 1688 |
| 23.4 | 1670 |
| 23.6 | 1628 |
| 23.8 | 1529 |
| 24 | 1582 |
| 24.2 | 1532 |
| 24.4 | 1514 |
| 24.6 | 1499 |
| 24.8 | 1476 |
| 25 | 1367 |
| 25.2 | 1360 |
| 25.4 | 1341 |
| 25.6 | 1237 |
| 25.8 | 1251 |
| 26 | 1187 |
| 26.2 | 1164 |
| 26.4 | 1133 |
| 26.6 | 1121 |
| 26.8 | 1073 |
| 27 | 1018 |
| 27.2 | 1007 |
| 27.4 | 1013 |
| 27.6 | 978 |
| 27.8 | 914 |
| 28 | 918 |
| 28.2 | 867 |
| 28.4 | 849 |
| 28.6 | 831 |
| 28.8 | 807 |
| 29 | 822 |
| 29.2 | 791 |
| 29.4 | 768 |
| 29.6 | 747 |
| 29.8 | 657 |
| 30 | 748 |
| 30.2 | 701 |
| 30.4 | 692 |
| 30.6 | 697 |
| 30.8 | 716 |

TABLE 1-continued

The X-ray diffractive spectrum of amorphous cefuroxime axetil obtained in the present invention:

| Angle (2θ) | Intensity |
|---|---|
| 31 | 622 |
| 31.2 | 639 |
| 31.4 | 649 |
| 31.6 | 683 |
| 31.8 | 624 |
| 32 | 657 |
| 32.2 | 615 |
| 32.4 | 692 |
| 32.6 | 629 |
| 32.8 | 592 |
| 33 | 606 |
| 33.2 | 619 |
| 33.4 | 607 |
| 33.6 | 616 |
| 33.8 | 582 |
| 34 | 550 |
| 34.2 | 564 |
| 34.4 | 561 |
| 34.6 | 555 |
| 34.8 | 549 |
| 35 | 528 |
| 35.2 | 548 |
| 35.4 | 598 |
| 35.6 | 596 |
| 35.8 | 546 |
| 36 | 572 |
| 36.2 | 512 |
| 36.4 | 503 |
| 36.6 | 519 |
| 36.8 | 545 |
| 37 | 479 |
| 37.2 | 530 |
| 37.4 | 496 |
| 37.6 | 530 |
| 37.8 | 537 |
| 38 | 514 |
| 38.2 | 483 |
| 38.4 | 515 |
| 38.6 | 511 |
| 38.8 | 498 |
| 39 | 496 |
| 39.2 | 542 |
| 39.4 | 507 |
| 39.6 | 483 |
| 39.8 | 468 |
| 40 | 437 |
| 40.2 | 508 |
| 40.4 | 518 |
| 40.6 | 434 |
| 40.8 | 518 |
| 41 | 447 |
| 41.2 | 388 |
| 41.4 | 488 |
| 41.6 | 470 |
| 41.8 | 473 |
| 42 | 466 |
| 42.2 | 462 |
| 42.4 | 442 |
| 42.6 | 482 |
| 42.8 | 469 |
| 43 | 461 |
| 43.2 | 454 |
| 43.4 | 448 |
| 43.6 | 442 |
| 43.8 | 419 |
| 44 | 418 |
| 44.2 | 445 |
| 44.4 | 436 |
| 44.6 | 406 |
| 44.8 | 367 |
| 45 | 390 |
| 45.2 | 400 |
| 45.4 | 429 |
| 45.6 | 405 |

TABLE 1-continued

| The X-ray diffractive spectrum of amorphous cefuroxime axetil obtained in the present invention: | |
|---|---|
| Angle (2θ) | Intensity |
| 45.8 | 408 |
| 46 | 414 |
| 46.2 | 433 |
| 46.4 | 387 |
| 46.6 | 389 |
| 46.8 | 385 |
| 47 | 398 |
| 47.2 | 386 |
| 47.4 | 386 |
| 47.6 | 403 |
| 47.8 | 387 |
| 48 | 360 |
| 48.2 | 361 |
| 48.4 | 377 |
| 48.6 | 349 |
| 48.8 | 337 |
| 49 | 357 |
| 49.2 | 348 |
| 49.4 | 331 |
| 49.6 | 313 |
| 49.8 | 290 |
| 50 | 342 |

The process of the present invention and the characteristics, features and advantages of the cefuroxime axetil particles obtained by the present process will be appreciated by those skilled in the art, with reference to the attached drawings and the following specific examples.

The liquid-liquid high-gravity reactor as shown in FIG. 1 was used in one of the examples in the invention. The schematic representation of the rotary bed was disclosed in Chinese patent No. 02127654.4, which is incorporated herein by reference in its entirety.

As illustrated in FIG. 1, upon starting up the high-gravity rotary packed bed, packing 3 is driven to rotate by rotor 2. The cefuroxime axetil solution and the antisolvent are contacted with each other instantaneously, and then precipitate and crystallize, upon feeding the cefuroxime axetil solution into the reactor via inlet 4 and spraying into packing 3 via the liquid distributor, and upon feeding the antisolvent into packing 3 via inlet 5. During the process of precipitating and crystallizing, the precipitated mixture from the packing 3 exits out of high-gravity rotary bed reactor via outlet 1. The temperature for precipitating can be adjusted within the range of between about −25° C. to about 95° C. by means of recycling water, and the ratio of solution to the antisolvent can be varied from between about 1:2 to about 1:40. Amorphous cefuroxime axetil can be obtained by filtering the slurry exiting from the high-gravity reactor, then washing and drying the filtrate.

According to the process of the invention, the flow rates of the materials involved in the process of precipitating and crystallizing in the high-gravity reactor are such that the reactants of the cefuroxime axetil solution and the antisolvent are able to enter into the reactor in a fashion to provide continuous and sufficient contact between the materials. During the preparation, the flow rates of the solution and the antisolvent are usually determined based on the different solvent systems. Typically the lowest outlet flow rate is above about 5 m/s in the high-gravity reactor. The solution and antisolvent can be separately fed into the high-gravity reactor with a respective flow rate as determined based on the specific high-gravity reaction apparatus.

For example, for the chloroform and isopropyl ether or ethyl ether system, the ratio of flow rates between the solution of cefuroxime axetil in chloroform and isopropyl ether or ethyl ether is within the range from between about 1:4 to about 1:50 (in volume), preferably from between about 1:10 to about 1:30. The flow rate of the solution of cefuroxime axetil in chloroform is within the range from between about 0.01 to about 0.06 $m^3$/hour, while that of isopropyl ether or ethyl ether is within the range from between about 0.04 to about 0.18 $m^3$/hour. When precipitation is complete, the slurry is filtered, washed, and dried immediately to obtain the desired ultrafine cefuroxime axetil powder in an amorphous form.

The invention will be further illustrated with reference to the following examples; however those examples are only illustrative of the invention and not intended to limit the scope thereof. The raw materials of cefuroxime axetil in its crystalline form are used in the examples, which can be commercially available, or can be prepared by the methods disclosed in GB 1,571,683 A1 or Chinese patent applications No. 01814420.9 (publication number 1447812A), which are all incorporated herein by reference.

EXAMPLES

Example 1

Figure 6:
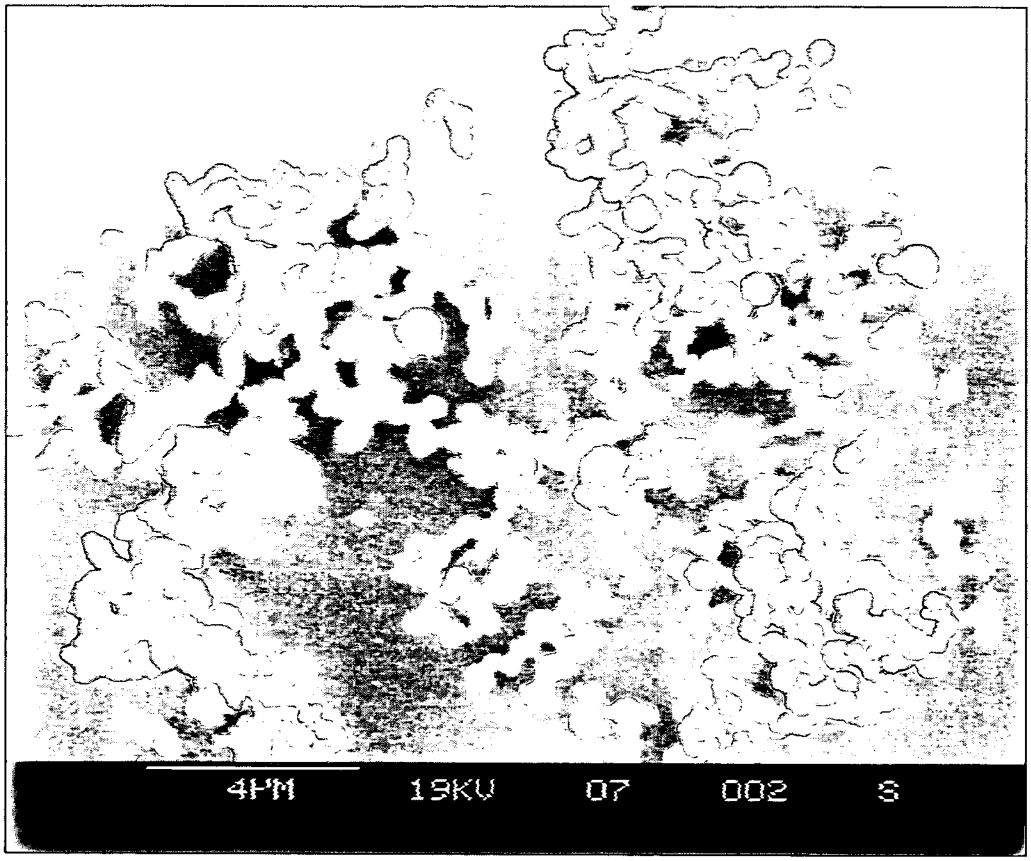
FIG. 6 shows an SEM image of the amorphous cefuroxime axetil prepared by the chloroform-isopropyl ether system according to the present invention.

1500 ml of the solution of crystalline cefuroxime axetil (200 g) in chloroform was put in a first tank, while 9 liters of isopropyl ether was put in a second tank. The two liquids were separately pumped through inlets 4 and 5 (FIG. 1), and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the cefuroxime axetil particles which were determined to be in an amorphous form as illustrated by the X-ray diffractive spectrum in FIG. 3. In the operation, the ratio of flow rates between the solution of cefuroxime axetil and isopropyl ether was about 1:6, with the rotating speed of the rotary packed bed at 1500 rpm. It can be seen from the SEM image as illustrated in FIG. 6 that the cefuroxime axetil particles had an average particle size of about 500 nm, and at least 70% of the particles had a particle size ranging from 300 nm to 400 nm.

Example 2

Figure 7:
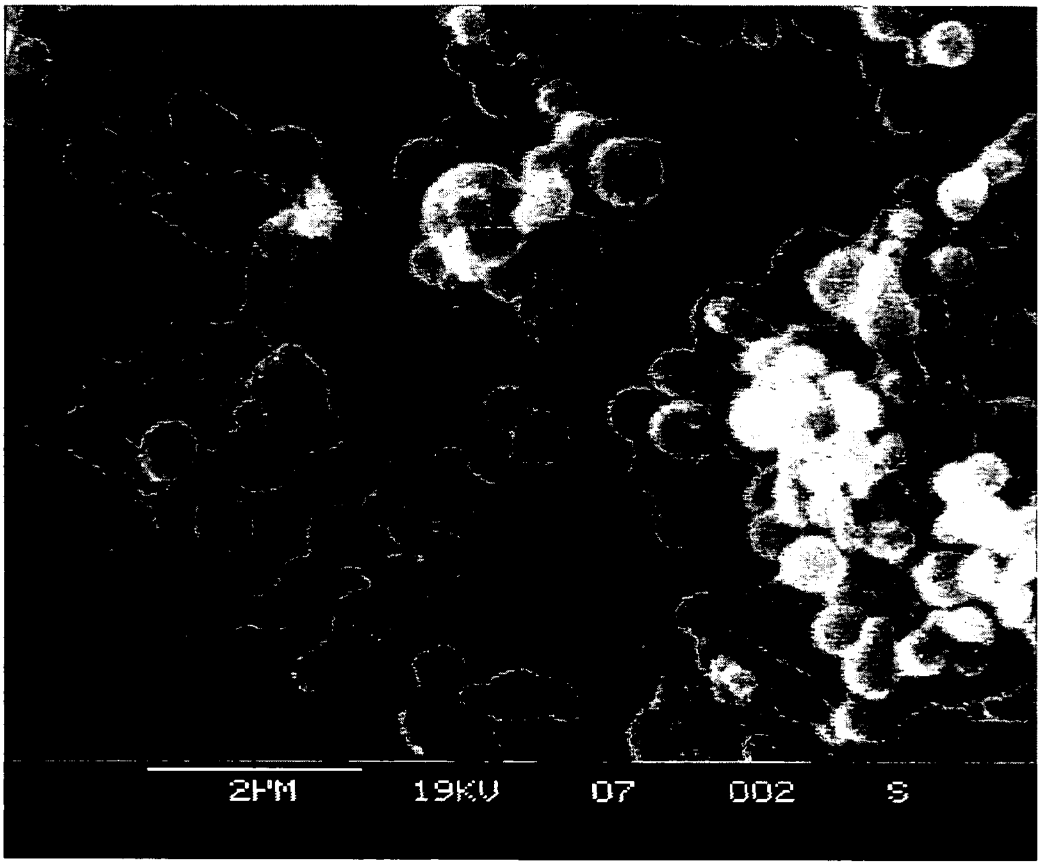
FIG. 7 shows an SEM image of the amorphous cefuroxime axetil prepared by the acetone-isopropyl ether system according to the present invention.

2000 ml of the solution of crystalline cefuroxime axetil (300 g) in acetone was put in a first tank, while 20 liters of isopropyl ether was put in a second tank. The two liquids were separately pumped through the inlets 4, 5 (FIG. 1), and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the ultrafine amorphous cefuroxime axetil particles. It can be seen from the SEM image as illustrated in FIG. 7 that the cefuroxime axetil particles had an average particle size of about 600 nm, and at least 70% of the particles had a particle size ranging from 400 nm to 600 nm. In the operation, the ratio of flow rates between the solution of cefuroxime axetil and isopropyl ether was about 1:10, with the rotating speed of the rotary packed bed at 2140 rpm.

Example 3

Before the example is performed, the high-gravity reactor was examined that it was running normally, and the speed of the rotary bed was changed to be 600 rpm by adjusting the frequency of the frequency modulator to be 10 Hz. 3000 ml of the solution of crystalline cefuroxime axetil (300 g) in N,N-dimethyl formamide was put in a first tank, while 45 liters of isopropyl ether was put in a second tank. The two liquids were separately pumped through the inlets 4, 5 (FIG. 1), and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried, to produce the ultrafine amorphous cefuroxime axetil particles. The cefuroxime axetil particles had an average particle size of about 1 μm. In the operation, the ratio of flow rates between the solution of cefuroxime axetil and isopropyl ether was about 1:15.

Example 4

2000 ml of the solution of cefuroxime axetil in chloroform with a concentration of 0.1 g/ml was formulated. 10 liters of ethyl ether was added into the stirred vessel as the antisolvent. The solution of cefuroxime axetil in chloroform was fed through the inlet, and then atomized by the orifice, followed by the rapid mixing with the antisolvent with a stirring speed of 1000 rpm. A white precipitate of cefuroxime axetil was obtained. The resultant slurry was immediately filtrated and the filtrate was washed and dried to produce the ultrafine amorphous cefuroxime axetil particles. The cefuroxime axetil particles had an average particle size of about 400 nm, and at least 90% of the particles had a particle size ranging from 300 nm to 400 nm.

Example 5

2000 ml of the solution of crystalline cefuroxime axetil (300 g) in chloroform was put in a first tank, while 40 liters of isopropyl ether was put in a second tank. The two liquids were separately pumped through the inlets 4, 5 (FIG. 1), and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the ultrafine cefuroxime axetil particles. The cefuroxime axetil particles had an average particle size of about 200 nm, and at least 70% of the particles had a particle size ranging from 100 nm to 200 nm. In the operation, the ratio of flow rates between the solution of cefuroxime axetil and isopropyl ether was about 1:20, with the rotating speed of the rotary packed bed at 2140 rpm.

Example 6

1000 ml of the solution of cefuroxime axetil in formic acid with a concentration of 0.3 g/ml was formulated. 15 liters of water was added into the stirred vessel as the antisolvent. The solution of cefuroxime axetil in formic acid was fed through inlet 4 (FIG. 1) and then atomized by the orifice, followed by the rapid mixing with the antisolvent with a stirring speed of 1000 rpm. A white precipitate of cefuroxime axetil was obtained. The resultant mixture was immediately filtrated, and the filtrate was washed and dried under vacuum at 60° C. to produce the ultrafine amorphous cefuroxime axetil particles. The cefuroxime axetil particles had an average particle size of about 1 μm. In the operation the ratio of flow rates between the solution of cefuroxime axetil and water was about 1:15.

Example 7

Figure 8:
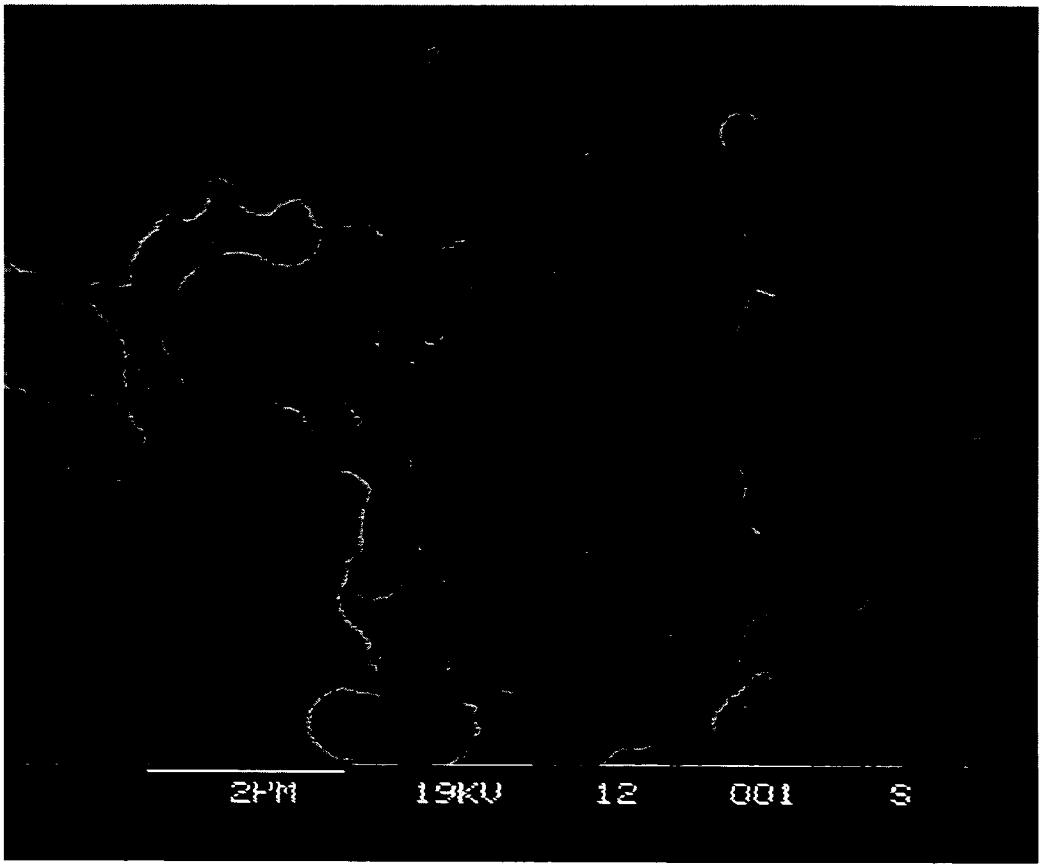
FIG. 8 shows an SEM image of the amorphous cefuroxime axetil prepared by the ethyl acetate-isopropyl ether system according to the present invention.

1000 ml of the solution of crystalline cefuroxime axetil (100 g) in ethyl acetate was put in a first tank, while 5 liters of isopropyl ether was put in a second tank. The two liquids were separately pumped through the inlets 4, 5 (FIG. 1) and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the ultrafine amorphous cefuroxime axetil particles. It can be seen from the SEM image as illustrated in FIG. 8 that the cefuroxime axetil particles had an average particle size of about 500 nm, and at least 90% of the particles had a particle size ranging from 300 nm to 500 nm. In the operation, the ratio of flow rates between the solution of cefuroxime axetil and isopropyl ether was about 1:5, with the rotating speed of the rotary bed at 1000 rpm.

Example 8

2000 ml of the solution of crystalline cefuroxime axetil in acetone (with a concentration of 0.08 g/ml) was put in a first tank, while 40 liters of de-ionized water was put in a second tank. The two liquids were separately pumped through the inlets 4, 5 (FIG. 1) and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the ultrafine amorphous cefuroxime axetil particles. The cefuroxime axetil particles had an average particle size of about 2 μm, and at least 90% of the particles had a particle size ranging from 1 μm nm to 2 μm. In the operation, the ratio of flow rates between the solution of cefuroxime axetil and water was about 1:20, with the rotating speed of the rotary bed at 600 rpm.

Example 9

1000 ml of the solution of cefuroxime axetil in acetone with a concentration of 0.1 g/ml was formulated. 15 liters of isopropyl ether at a temperature of 5° C. was added into the stirred vessel as the antisolvent. The solution of cefuroxime axetil in acetone was added into the isopropyl ether via the orifice of the atomizer, and mixed rapidly with isopropyl ether. A white precipitate of cefuroxime axetil was immediately obtained. The resultant slurry of cefuroxime axetil was immediately filtrated and the filtrate was washed and dried under vacuum at 60° C. to produce the ultrafine amorphous cefuroxime axetil particles. The cefuroxime axetil particles had an average particle size of about 500 nm. In the operation, the ratio of flow rates between the solution of cefuroxime axetil and isopropyl ether water was about 1:15, with the rotating speed of the rotary bed at 1000 rpm.

Example 10

3000 ml of the solution of crystalline cefuroxime axetil (300 g) in chloroform was put in a first tank, while 45 liters of isopropyl ether at a temperature of 0° C. was put in a second tank. The two liquids were separately pumped through the inlets 4, 5 (FIG. 1) and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed. The slurry was filtrated, and the filtrate was washed and dried to produce the ultrafine amorphous cefuroxime axetil particles. The cefuroxime axetil particles had an average particle size of about 600 nm. In the operation, the ratio of flow rates between the solution of cefuroxime axetil and isopropyl ether was about 1:15, with the rotating speed of the rotary packed bed at 2140 rpm.

Example 11

1000 ml of the solution of crystalline cefuroxime axetil (100 g) in chloroform was put in a first tank, while 20 liters of ethyl ether was put in a second tank. Recycling water of 50 ° C. was used to heat the two liquids in the tanks, respectively, and recycling water of 50 ° C. was circulated through the jacket of the rotary packed bed, so as to heat the packing layer of the rotary bed. The two liquids were separately pumped through the inlets 4, 5 (FIG. 1) and then sprayed into the packing layer 3 in the rotary packed bed via liquid distributors at ambient temperature. The two liquids were then subjected to precipitation and crystallization after being mixed with each other rapidly and effectively within the packing layer. A white precipitate of cefuroxime axetil was obtained, which was then discharged through the outlet 1 of the rotary bed and then filtrated. The filtrate was washed and dried to produce the ultrafine amorphous cefuroxime axetil particles. The cefuroxime axetil particles had an average particle size of about 1 μm.

Figure 4:
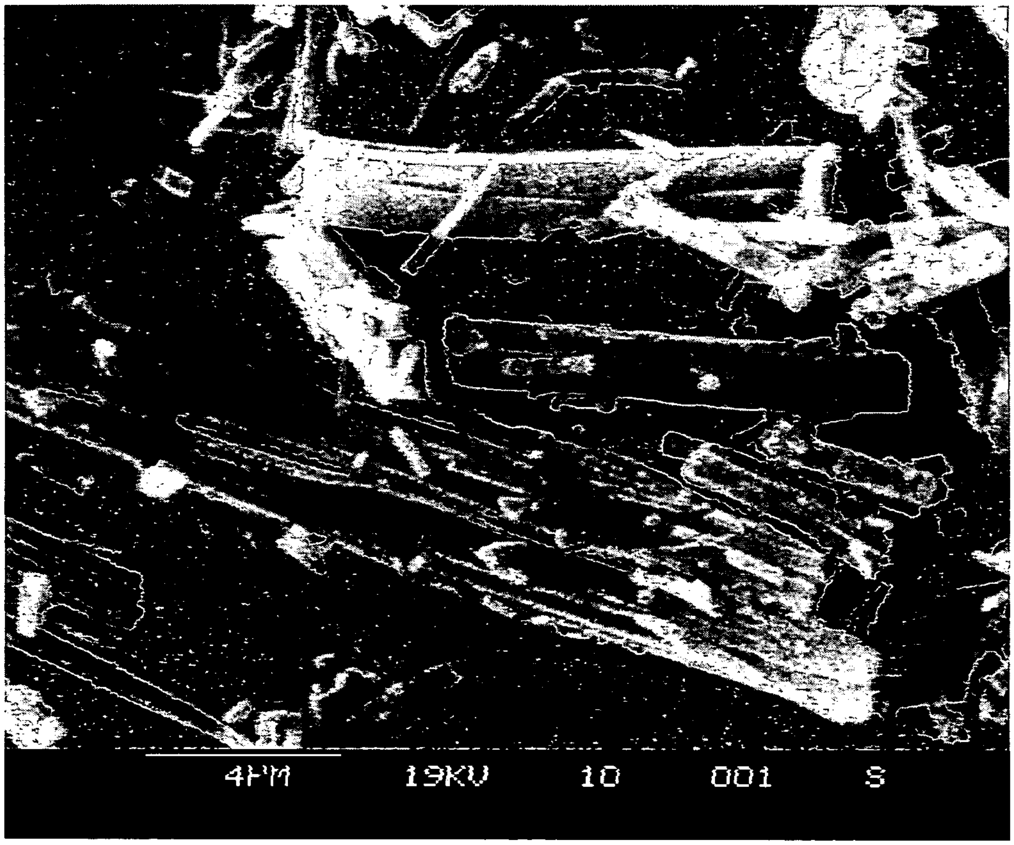
FIG. 4 shows an SEM (Scanning Electron Microscope) image of the cefuroxime axetil prepared by the conventional method.
Figure 5:
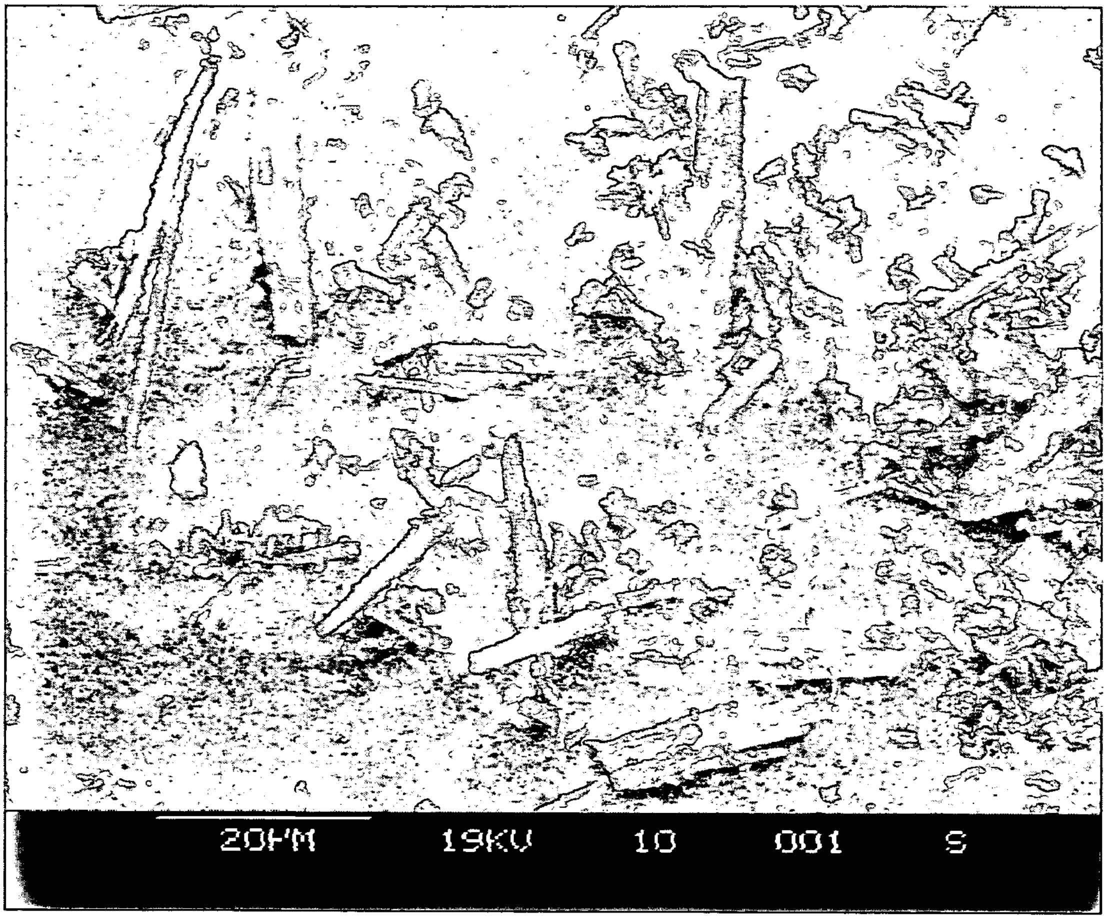
FIG. 5 shows an SEM image of the cefuroxime axetil prepared by a conventional method.

It can be seen from the above description in combination with the specific result data and the drawings that a ultrafine cefuroxime axetil powder can be prepared by precipitating and crystallizing with the help of an antisolvent within the stirred vessel or high-gravity reactor. The resultant powders, seen in FIGS. 6-8, are significantly smaller and more uniform than those particles in the conventional crystalline form, seen in FIGS. 4 and 5. In addition, the average particle size of the particles can be controlled, if desired. The particles have a narrow and uniform particle size distribution, leading to unexpected effects. In particular, the requirement of pulverization treatment under special condition is avoided.

In comparison to the standards of "2000 Chinese pharmacopeias" (the second edition), all the results of the ultrafine cefuroxime axetil in an amorphous form according to the invention conformed perfectly. SEM images show that the particle size was approximately 300 to 500 nm. Also, the amorphous form of cefuroxime axetil had a higher bioavailability than its crystalline form. Therefore, the present invention provides a cefuroxime axetil particle with a controllable average particle size and narrow particle distribution, particularly an ultrafine or even nanosized amorphous cefuroxime axetil particle, more particularly an ultrafine or even nanosized cefuroxime axetil particle with a controllable average particle size and narrow particle distribution.

In preparing amorphous cefuroxime axetil particles by means of the antisolvent precipitation in the stirred vessel reactor, the liquid is immediately atomized into very small droplets due to a special feeding inlet. The solution and antisolvent are mixed rapidly under high-speed stirring to facilitate a uniform concentration distribution within the whole stirred vessel, thus avoiding the presence of local non-uniformity and supersaturation, and also agglomeration and adhesive bonding of cefuroxime axetil particles. Consequently, the quality and grade of the amorphous cefuroxime axetil is improved. The reaction can also be carried out by appropriately increasing the temperature or without the use of low temperature. Moreover, the yield ratio was enhanced significantly.

In preparing amorphous cefuroxime axetil by means of the antisolvent precipitation in the high-gravity reactor, the solution and antisolvent are sufficiently contacted with each other, thus avoiding the presence of local non-uniformity and supersaturation, and also agglomeration and adhesive bonding of cefuroxime axetil particles. Consequently, by use of the high-gravity reactor, the reaction is facilitated, and the reaction time is decreased. The reaction can also be carried out with appropriately increasing the temperature or without the use of low temperature. Moreover, the yield ratio was enhanced significantly.

The ultrafine amorphous cefuroxime axetil prepared by the method described in this invention has many advantages, such as small particle size, uniformity, narrow particle size distribution, good fluidity, and so on. In medical applications, it brings about unexpected effects on, for example, bioavailability and solubility over the prior art.

While the present invention has been illustrated by the description of embodiments and examples thereof, and while the embodiments and examples have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative methods and structures, and illustrated examples shown and described. Accordingly, numerous alternative embodiments will be apparent to those skilled in the art without departing from the scope or spirit of the general inventive concept.

What is claimed is:

1. A process for the preparation of amorphous cefuroxime axetil having an average particle size of between about 20 nm to about 30 μm, comprising the steps of:

(a) providing a cefuroxime axetil solution and a suitable antisolvent;

(b) spraying the cefuroxime axetil solution via an atomizer into a stirred reactor which contains the antisolvent, thereby precipitating and crystallizing the cefuroxime axetil into a slurry via antisolvent recrystallization;

(c) collecting the slurry of cefuroxime axetil obtained in step (b); and (d) filtering and then drying the filtered slurry of cefuroxime axetil to obtain cefuroxime axetil powder in an amorphous form wherein the cefuroxime axetil powder has an average particle size of between about 20 nm to about 30 μm.

2. The process of claim 1, wherein the cefuroxime axetil solution is formed by dissolving cefuroxime axetil in a solvent selected from the group consisting of methanol, dichloromethane, chloroform, acetone, ethyl acetate, formic acid, acetic acid, dioxane, dimethyl sulfoxide, N,N-dimethyl formamide, and mixtures thereof.

3. The process of claim 1, wherein the antisolvent is selected from the group consisting of isopropyl ether, methyl tert-butyl ether, ethyl ether, n-hexane, water, and mixtures thereof.

4. The process of claim 1, wherein the cefuroxime axetil solution is selected from the group consisting of a solution of cefuroxime axetil in ethyl acetate, a solution of cefuroxime axetil in acetone, a solution of cefuroxime axetil in chloroform, and mixtures thereof.

5. The process of claim 4, wherein the cefuroxime axetil solution is a solution of cefuroxime axetil in acetone.

6. The process of claim 1, wherein the stirred reactor operates at a stirred speed ranging from between about 50 rpm to about 10,000 rpm.

7. The process of claim 1, wherein the ratio of the cefuroxime axetil solution to the antisolvent is between about 1:5 and about 1:50.

8. The process of claim 1, wherein the ratio of the cefuroxime axetil solution to the antisolvent is between about 1:10 and about 1:30.

* * * * *